(12) United States Patent
Amino et al.

(10) Patent No.: US 9,295,624 B2
(45) Date of Patent: Mar. 29, 2016

(54) AMIDE DERIVATIVE AND WHITENING AGENT

(71) Applicant: AJINOMOTO CO. INC., Tokyo (JP)

(72) Inventors: Yusuke Amino, Kawasaki (JP); Yoshinobu Takino, Kawasaki (JP); Satoru Ohashi, Kawasaki (JP); Fumie Okura, Kawasaki (JP); Megumi Kaneko, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/287,899

(22) Filed: May 27, 2014

(65) Prior Publication Data

US 2014/0255327 A1 Sep. 11, 2014

Related U.S. Application Data

(60) Division of application No. 13/240,358, filed on Sep. 22, 2011, now abandoned, which is a continuation of application No. PCT/JP2010/055162, filed on Mar. 25, 2010.

(30) Foreign Application Priority Data

Mar. 25, 2009 (JP) ................................. 2009-075006

(51) Int. Cl.
| | |
|---|---|
| *A61K 31/4045* | (2006.01) |
| *C07D 209/32* | (2006.01) |
| *A61K 8/49* | (2006.01) |
| *A61K 8/42* | (2006.01) |
| *A61Q 19/02* | (2006.01) |
| *C07C 235/34* | (2006.01) |
| *C07D 209/14* | (2006.01) |
| *C07D 209/20* | (2006.01) |
| *C07D 405/12* | (2006.01) |

(52) U.S. Cl.
CPC . *A61K 8/492* (2013.01); *A61K 8/42* (2013.01); *A61K 8/49* (2013.01); *A61K 31/4045* (2013.01); *A61Q 19/02* (2013.01); *C07C 235/34* (2013.01); *C07D 209/14* (2013.01); *C07D 209/20* (2013.01); *C07D 209/32* (2013.01); *C07D 405/12* (2013.01)

(58) Field of Classification Search
CPC .......................... A61K 31/4045; C07D 209/32
See application file for complete search history.

(56) References Cited

U.S. PATENT DOCUMENTS

2007/0183996 A1 8/2007 Okombi et al.
2008/0171781 A1 7/2008 Katsuda et al.

FOREIGN PATENT DOCUMENTS

| JP | 08-053332 | 2/1996 |
|---|---|---|
| JP | 08-175959 | 7/1996 |
| JP | 2006-052152 | 2/2006 |
| JP | 2009-040688 | 2/2009 |
| WO | 2007/032551 | 3/2007 |

OTHER PUBLICATIONS

Ho et al. (J. Pharm. Sci., vol. 60, No. 4, Apr. 1971, p. 636-637).*
Office Action issued Jul. 22, 2014 in Japanese Patent Application No. 2011-506106 (with English language translation).
Colin J. Suckling, et al., "$M_4$agonists/$5HT_7$ antagonists with potential as antischizophrenic drugs: Serominic compounds", Bioorganic and Medicinal Chemistry Letters, vol. 17, 2007, pp. 2649-2655.
Demétrius Antonio Machado Araújo, et al., "$N$-salicyloyltryptamine, a new anticonvulsant drug, acts on voltage-dependent $Na^+$, $Ca^{2+}$, and $K^+$ ion channels", British Journal of Pharmacology, vol. 140, 2003, pp. 1331-1339.
Francisco A. Oliveira, et al., "Anticonvulsant properties of $N$-salicyloyltryptamine in mice", Pharmacology, Biochemistry, and Behavior, vol. 68, 2001, pp. 199-202.
Beng T. Ho, et al., "Hydroxyindole-$O$-methyltransferase VI: Inhibitory activities of substituted benzoyltryptamines and benzenesulfonyltryptamines", Journal of Pharmaceutical Sciences, vol. 60, No. 4, 1971, pp. 636-637 with cover page.
M. Protiva, et al., "Synthetische versuche in der gruppe hypotensiv wirksamer alkaloide XXV.* Einige 3-(2-benzylaminoäthyl)indole und 3-(2-phenoxyäthylamino)äthyl]indole**", Collection of Czechoslovak Chemical Communications, vol. 28, 1963, pp. 629-636 with cover page.
Funayama et al., "Bioscience, Biotechnoogy & Biochemistry", vol. 59, No. 1, (1995) pp. 143-144.
Miyazaki et al., "Journal of Japanese Cosmetic Science Society", vol. 22, No. 3, (1998) pp. 182-186.
"The Journal of Japan Hair Science Association", vol. 30, No. 3, (1998) pp. 2-6 and partial English translation.
Dong-Seok Kim et al., "Biological & Pharmaceutical Bulletin", vol. 28, No. 12, (2005), pp. 2216-2219.
Y. Yamazaki et al., "Biorganic & Medicinal Chemistry Letters", vol. 19, (2009) pp. 4178-4182.
Sabrina Okombi et al., "Bioorg. Med. Chem. Lett", vol. 16, (2006) pp. 2252-2255.
Sung J. Cho et al., "Bioorg. Med. Chem. Lett", vol. 16, (2006) pp. 2682-2684.

(Continued)

*Primary Examiner* — Robert Havlin
(74) *Attorney, Agent, or Firm* — Oblon, McClelland, Maier & Neustadt, L.L.P.

(57) ABSTRACT

Compound represented by formula (I):

wherein the symbols are as defined in the description, and salts thereof, are useful as skin whitening agents.

2 Claims, 5 Drawing Sheets

(56) References Cited

OTHER PUBLICATIONS

International Search Report issued in PCT/JP2010/055162 on Jun. 15, 2010.
Supplementary European Search Report issued Dec. 19, 2012 in U.S. Appl. No. 10/756,149.
Stanley Juan C. Gutierrez et al., "Nb-benzoyltryptamine Derivatives with Relaxant Activity in Guinea-pig Ileum", IL Farmaco, Elsevier France * Editions Scientifiques et Medicales, vol. 60, No. 6-7, XP-027697570, Jun. 1, 2005, pp. 475-477.
Kiyoon Kang et al., "Production of Phenylpropanoid Amides in Recombinant *Escherichia coli*", Metabolic Engineering, vol. 11, No. 1, XP-025656321, Jan. 1, 2009, pp. 64-68.

M. Protiva et al., "Synthetic Experiments with Hypotensive Alkaloids. XXV. 3-(2-Benzylaminoethyl) Indole and 3- [2-(2-phenoxyethylamino) Ethyl] Indole Derivatives", Database CA [Online] Chemical Abstracts Service, AN-1963:435473, XP-002689552, 1963, 2 pages.
Wermuth, The Practice of Medicinal Chemistry, $2^{nd}$ ed. 2003, Elsevier, 768 pages. Chs. 12-13 provided.
Cannon, "Analog Design" in Burger's Medicinal Chemistry and Drug Discovery, 6th ed. 2003, Wiley, pp. 687-714.
Sakamura et al. (CAPLUS Abstract of: Agricultural and Biological Chemistry (1978), 42(9), 1805-6).

* cited by examiner

AMIDE DERIVATIVE AND WHITENING AGENT

CROSS REFERENCES TO RELATED APPLICATIONS

This application is a continuation of International Patent Application No. PCT/JP2010/055162, filed on Mar. 25, 2010, and claims priority to Japanese Patent Application No. 2009-075006, filed on Mar. 25, 2009, both of which are incorporated herein by reference in their entireties.

BACKGROUND OF THE INVENTION

1. Field of the Invention

The present invention relates to novels compound having a melanin production suppressive activity. The present invention also relates to the use of such a compound in the field of cosmetics.

2. Discussion of the Background

Hydroquinone glycoside (arbutin) is known to have various effects such as a whitening effect, tyrosinase inhibitory activity, suppression of active oxygen, and the like (see Funayama, M., Arakawa, H., Yamamoto, R., Nishino, T., Shin, T. and Murao, S., "Effect of α- and β-arubutin on activity of tyrosinases from mushroom, and mouse melanoma," *Biosci. Biotech. Biochem.*, vol. p. 59, 143-144 (1995)), and is used as an ingredient for whitening cosmetics. In addition, kojic acid or a derivative thereof and 4-n-butyl-resorcinol (Rucinol (registered trade mark)) are also known as whitening components (see Kouji Miyazaki, Yumiko Nishida, Minoru Itioka, "Inhibitory Effects of Melanogenic Inhibitors on Dendricity of Cultured B16 Mouse Melanoma Cells," *Journal of Japanese Cosmetic Science Society*, vol. 22, No. 3, pp. 182-186 (1998); Kiyoharu Sugiyama, "Evaluation of novel whitening agent—Rucinol (*Shinki bihakuzai no hyouka—Rucinol ni tsuite*)," *The Journal of Japan Hair Science Association*, vol. 30, No. 3, pp. 2-6 (1998); and Dong-Seok KIM, So-Young KIM, Seo-Hyoung PARK, Yeong-Gon CHOI, Sun-Bang KWON, Myo-Kyoung KIM, Jung-Im Na, Sang-Woong YOUN, and Kyoung-Chan PARK, "Inhibitory Effects of 4-n-Butylresorcinol on Tyrosinase Activity and Melanin Synthesis," *Biol. Pharm. Bull.*, vol. 28(12), pp. 2216-2219 (2005)), and whitening cosmetics containing such components are commercially available. In recent years, prevention of sunburn due to ultraviolet rays to keep the skin white and beautiful is receiving increasing attention, and the development of a further whitening component is desired.

SUMMARY OF THE INVENTION

Accordingly, it is one object of the present invention to provide novel compound having a melanin production suppressive activity, and the like.

It is another object of the present invention to provide novel cosmetics which contain such a compound.

These and other objects, which will become apparent during the following detailed description, have been achieved by the inventors' discovery of novel compounds which have a melanin production suppressive activity, and the like.

Thus, the present invention provides the following:
(1) A compound represented by the following formula (I):

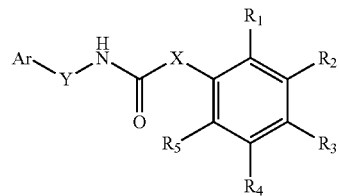

wherein $R_1$, $R_2$, $R_3$, $R_4$ and $R_5$ are each independently a hydrogen atom, an alkyl group having a carbon number of 1 to 3, a hydroxyl group or an alkoxy group having a carbon number of 1 to 3, or $R_1$ and $R_2$, or $R_2$ and $R_3$ in combination optionally form a methylenedioxy group;
X is a covalent bond, a methylene group, an ethylene group or a vinylene group;
Y is a covalent bond or a divalent group represented by the formula:

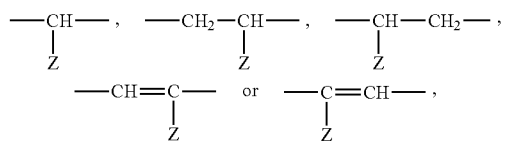

Z is a hydrogen atom, a hydroxycarbonyl group or an alkoxycarbonyl group having a carbon number of 1 to 3, and when Z is other than a hydrogen atom and a carbon atom bonded to Z contains an asymmetric center, the stereochemistry thereof may be any of (S), (R) and (SR);
Ar is a substituent represented by the following formula (II):

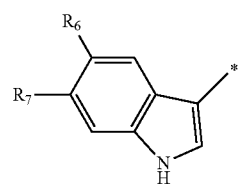

wherein $R_6$ and $R_7$ are each independently a hydrogen atom, an alkyl group having a carbon number of 1 to 3, a hydroxyl group or an alkoxy group having a carbon number of 1 to 3, and * is a moiety bonded to Y, or
the following formula (III):

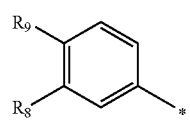

wherein $R_8$ and $R_9$ are each independently a hydrogen atom, an alkyl group having a carbon number of 1 to 3, a hydroxyl group or an alkoxy group having a carbon number of 1 to 3, or $R_8$ and $R_9$ in combination optionally form a methylenedioxy group, and * is a moiety bonded to Y;

provided that the following compounds are excluded:

(1) a compound wherein, when Ar is a substituent m represented by the formula (II), X is a vinylene group, Y is an ethylene group, $R_1$, $R_2$, $R_5$ and $R_7$ are hydrogen atoms, and $R_6$ is a hydroxyl group, then $R_3$ is a hydroxyl group and $R_4$ is a hydrogen atom, or $R_3$ is a hydroxyl group and $R_4$ is a methoxy group, or $R_3$ and $R_4$ are hydroxyl groups, or $R_3$ is a methoxy group and $R_4$ is a hydroxyl group, or $R_3$ is a methoxy group and $R_4$ is a hydrogen atom;

(2) a compound wherein, when Ar is a substituent represented by the formula (II), X is a vinylene group, Y is an ethylene group, and $R_1$, $R_2$, $R_5$, $R_6$ and $R_7$ are hydrogen atoms, then $R_3$ is a hydroxyl group and $R_4$ is a hydrogen atom, or $R_3$ is a methoxy group and $R_4$ is a hydrogen atom, or $R_3$ and $R_4$ are hydroxyl groups, or $R_3$ is a hydroxyl group and $R_4$ is a methoxy group;

(3) a compound wherein, when Ar is a substituent represented by the formula (II), X is a vinylene group, Y is an ethylene group, $R_1$, $R_2$, $R_5$ and $R_7$ are hydrogen atoms, and $R_6$ is a methoxy group, then $R_3$ is a hydroxyl group and $R_4$ is a hydrogen atom, or $R_3$ is a methoxy group and $R_4$ is a hydrogen atom, or $R_3$ and $R_4$ are hydrogen atoms;

(4) a compound wherein, when Ar is a substituent represented by the formula (II), X is a covalent bond, Y is an ethylene group, $R_1$, $R_2$, $R_5$ and $R_7$ are hydrogen atoms, and $R_6$ is a hydroxyl group, then $R_3$ and $R_4$ are hydroxyl groups, or $R_3$ is a hydroxyl group and $R_4$ is a methoxy group, or $R_3$ and $R_4$ are hydrogen atoms, or $R_3$ is a methoxy group and $R_4$ is a hydrogen atom; and (5) a compound wherein Ar is a substituent represented by the formula (III), Y is an ethylene group, and one or both of $R_8$ and $R_9$ is/are a hydrogen atom(s);
or a salt thereof.

(2) A compound represented by the following formula (IV):

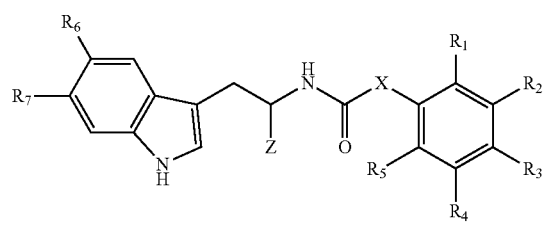

wherein $R_1$, $R_2$, $R_3$, $R_4$, $R_5$, $R_6$ and $R_7$ are each independently a hydrogen atom, an alkyl group having a carbon number of 1 to 3, a hydroxyl group or an alkoxy group having a carbon number of 1 to 3, or $R_1$ and $R_2$, or $R_2$ and $R_3$ in combination optionally form a methylenedioxy group;
X is a methylene group, an ethylene group or a vinylene group;
Z is a hydrogen atom, a hydroxycarbonyl group or an alkoxycarbonyl group having a carbon number of 1 to 3; and
when Z is other than a hydrogen atom, the stereochemistry of a carbon atom bonded to Z may be any of (S), (R) and (SR);
provided that the following compounds are excluded:

(1) a compound wherein, when X is a vinylene group, Z is a hydrogen atom, $R_1$, $R_2$, $R_5$ and $R_7$ are hydrogen atoms, and $R_6$ is a hydroxyl group, then $R_3$ is a hydroxyl group and $R_4$ is a hydrogen atom, or $R_3$ is a hydroxyl group and $R_4$ is a methoxy group, or $R_3$ and $R_4$ are hydroxyl groups, or $R_3$ is a methoxy group and $R_4$ is a hydroxyl group, or $R_3$ is a methoxy group and $R_4$ is a hydrogen atom;

(2) a compound wherein, when X is a vinylene group, Z is a hydrogen atom, and $R_1$, $R_2$, $R_5$, $R_6$ and $R_7$ are hydrogen atoms, then $R_3$ is a hydroxyl group and $R_4$ is a hydrogen atom, or $R_3$ is a methoxy group and $R_4$ is a hydrogen atom, or $R_3$ and $R_4$ are hydroxyl groups, or $R_3$ is a hydroxyl group and $R_4$ is a methoxy group; and (3) a compound wherein, when X is a vinylene group, Z is a hydrogen atom, $R_1$, $R_2$, $R_5$ and $R_7$ are hydrogen atoms, and $R_6$ is a methoxy group, then $R_3$ is a hydroxyl group and $R_4$ is a hydrogen atom, or $R_3$ is a methoxy group and $R_4$ is a hydrogen atom, or $R_3$ and $R_4$ are hydrogen atoms;
or a salt thereof.

(3) A compound represented by the following formula (V):

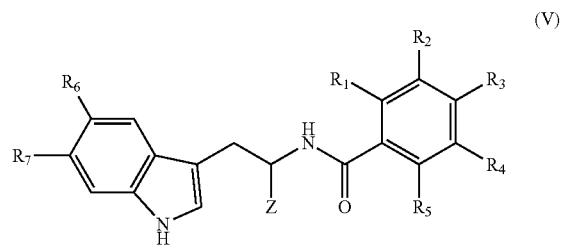

wherein $R_1$, $R_2$, $R_3$, $R_4$, $R_5$, $R_6$ and $R_7$ are each independently a hydrogen atom, an alkyl group having a carbon number of 1 to 3, a hydroxyl group or an alkoxy group having a carbon number of 1 to 3, or $R_1$ and $R_2$, or $R_2$ and $R_3$ in combination optionally form a methylenedioxy group;
Z is a hydrogen atom, a hydroxycarbonyl group or an alkoxycarbonyl group having a carbon number of 1 to 3, and when Z is other than a hydrogen atom, the stereochemistry of a carbon atom bonded to Z may be any of (S), (R) and (SR), provided that the following compound is excluded: a compound wherein, when Z is a hydrogen atom, $R_1$, $R_2$, $R_5$ and $R_7$ are hydrogen atoms, and $R_6$ is a hydroxyl group, then $R_3$ and $R_4$ are hydroxyl groups, or $R_3$ is a hydroxyl group and $R_4$ is a methoxy group, or $R_3$ and $R_4$ are hydrogen atoms, or $R_3$ is a methoxy group and $R_4$ is a hydrogen atom; or a salt thereof.

(4) A compound represented by the following formula (VI):

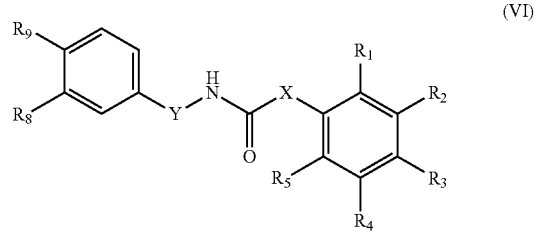

wherein $R_1$, $R_2$, $R_3$, $R_4$ and $R_5$ are each independently a hydrogen atom, an alkyl group having a carbon number of 1 to 3, a hydroxyl group or an alkoxy group having a carbon number of 1 to 3, or $R_1$ and $R_2$, or $R_2$ and $R_3$ in combination optionally form a methylenedioxy group;
X is a covalent bond, a methylene group, an ethylene group or a vinylene group;
Y is a covalent bond or a divalent group represented by the formula:

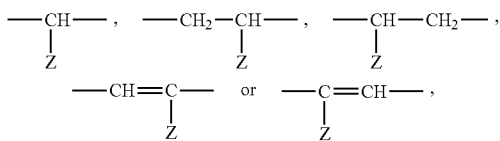

Z is a hydrogen atom, a hydroxycarbonyl group or an alkoxycarbonyl group having a carbon number of 1 to 3, and when Z is other than a hydrogen atom and a carbon atom bonded to Z contains an asymmetric center, the stereochemistry thereof may be any of (S), (R) and (SR);
$R_8$ and $R_9$ are each independently a hydrogen atom, an alkyl group having a carbon number of 1 to 3, a hydroxyl group or an alkoxy group having a carbon number of 1 to 3, or $R_8$ and $R_9$ in combination optionally form a methylenedioxy group, provided that the following compound is excluded: a compound wherein Y is an ethylene group, and one or both of $R_8$ and $R_9$ is/are a hydrogen atom(s);
or a salt thereof.

(5) A whitening agent, comprising a compound represented by the following formula (I'):

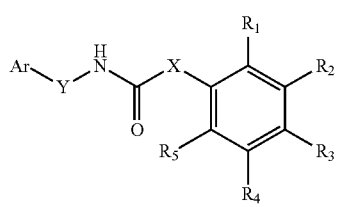

wherein $R_1$, $R_2$, $R_3$, $R_4$ and $R_5$ are each independently a hydrogen atom, an alkyl group having a carbon number of 1 to 3, a hydroxyl group or an alkoxy group having a carbon number of 1 to 3, or $R_1$ and $R_2$, or $R_2$ and $R_3$ in combination optionally form a methylenedioxy group;
X is a covalent bond, a methylene group, an ethylene group or a vinylene group;
Y is a covalent bond or a divalent group represented by the formula:

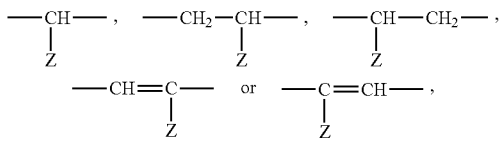

Z is a hydrogen atom, a hydroxycarbonyl group or an alkoxycarbonyl group having a carbon number of 1 to 3, and when Z is other than a hydrogen atom and a carbon atom bonded to Z contains an asymmetric center, the stereochemistry thereof may be any of (S), (R) and (SR);
Ar is a substituent represented by the following formula (II):

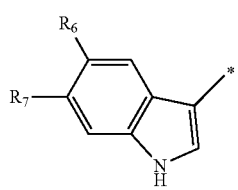

wherein $R_6$ and $R_7$ are each independently a hydrogen atom, an alkyl group having a carbon number of 1 to 3, a hydroxyl group or an alkoxy group having a carbon number of 1 to 3, and * is a moiety bonded to Y, or
the following formula (III):

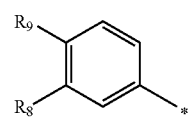

wherein $R_8$ and $R_9$ are each independently a hydrogen atom, an alkyl group having a carbon number of 1 to 3, a hydroxyl group or an alkoxy group having a carbon number of 1 to 3, or $R_8$ and $R_9$ in combination optionally form a methylenedioxy group, and * is a moiety bonded to Y;
provided that the following compounds are excluded:
(1) a compound wherein, when Ar is a substituent represented by the formula (II), X is a vinylene group, Y is an ethylene group, $R_1$, $R_2$, $R_5$ and $R_7$ are hydrogen atoms, and $R_6$ is a hydroxyl group, then $R_3$ is a hydroxyl group and $R_4$ is a hydrogen atom, or $R_3$ is a hydroxyl group and $R_4$ is a methoxy group, or $R_3$ and $R_4$ are hydroxyl groups;
(2) a compound wherein, when Ar is a substituent represented by the formula (II), X is a vinylene group, Y is an ethylene group, and $R_1$, $R_2$, $R_5$, $R_6$ and $R_7$ are hydrogen atoms, then $R_3$ and $R_4$ are hydroxyl groups;
(3) a compound wherein, when Ar is a substituent represented by the formula (II), X is a covalent bond, Y is an ethylene group, $R_1$, $R_2$, $R_5$ and $R_7$ are hydrogen atoms, and $R_6$ is a hydroxyl group, then $R_3$ and $R_4$ are hydroxyl groups, or $R_3$ is a hydroxyl group and $R_4$ is a methoxy group, or $R_3$ and $R_4$ are hydrogen atoms; and
(4) a compound wherein Ar is a substituent represented by the formula (III), Y is an ethylene group, $R_1$, $R_2$, $R_5$ and $R_8$ are hydrogen atoms, and $R_3$, $R_4$ and $R_9$ are hydroxyl groups;
or a salt thereof.

(6) A whitening agent comprising the compound of any of the aforementioned (1) to (4) or a salt thereof.

The compounds of the present invention are expected to exhibit a whitening action through a melanin production suppressive activity, and can be utilized as a whitening agent by itself or in combination with other whitening components.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
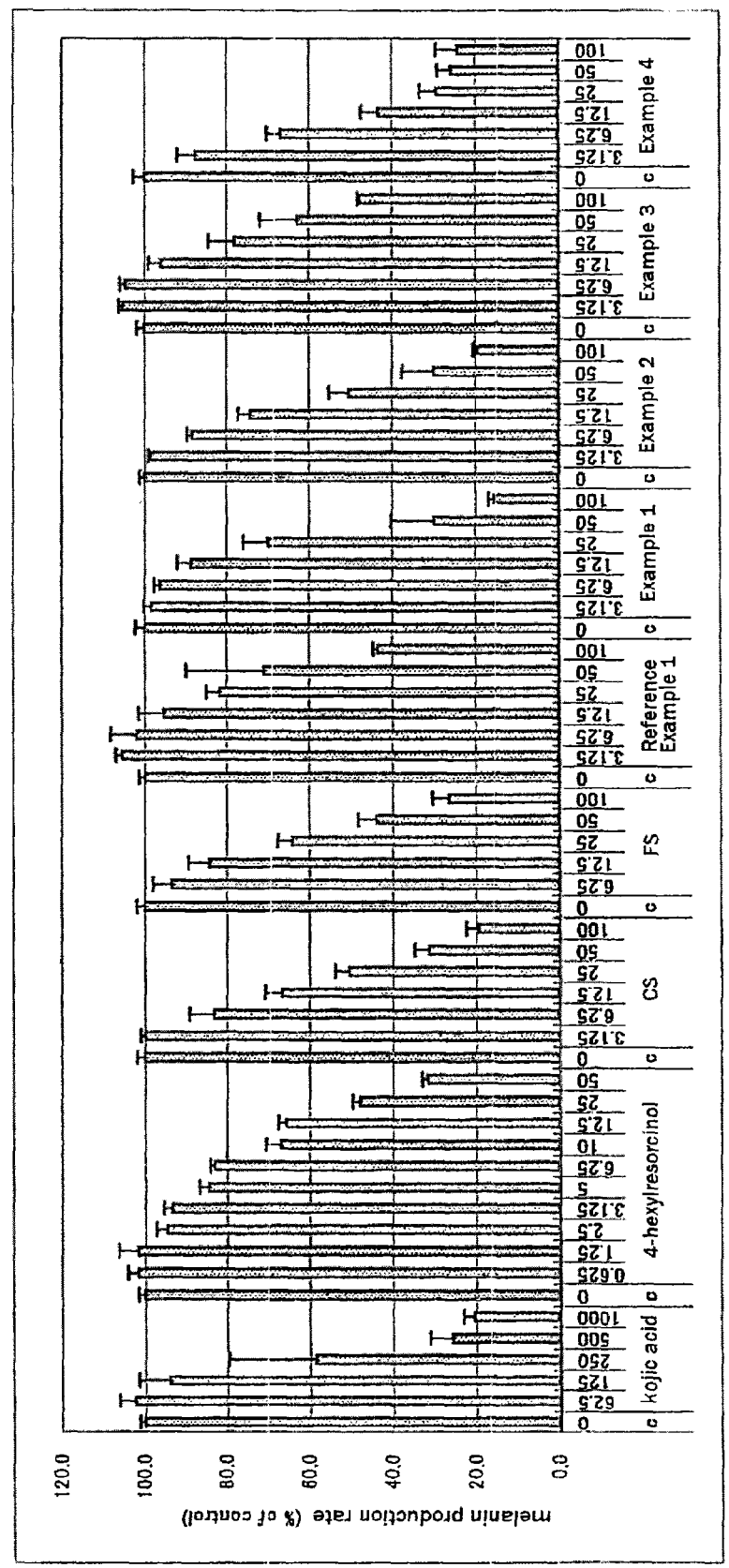
FIG. 1 is a graph showing the results of Experimental example 1. In the graph, the unit of the values on the horizontal axis is μM.

The definitions of the symbols in each formula used in the present specification are explained.

Examples of the alkyl group having a carbon number of 1 to 3 for $R_1$, $R_2$, $R_3$, $R_4$, $R_5$, $R_6$, $R_7$, $R_8$ or $R_9$ include a methyl group, an ethyl group, a propyl group and an isopropyl group. Of these, a methyl group is preferable.

Examples of the alkoxy group having a carbon number of 1 to 3 for $R_1$, $R_2$, $R_3$, $R_4$, $R_5$, $R_6$, $R_7$, $R_8$ or $R_9$ include a methoxy group, an ethoxy group, a propoxy group and an isopropoxy group. Of these, a methoxy group or an ethoxy group is preferable, and a methoxy group is more preferable.

The alkoxycarbonyl group having a carbon number of 1 to 3 means those compounds in which the alkoxy moiety has a carbon number of 1 to 3. Examples of the alkoxycarbonyl group having a carbon number of 1 to 3 for Z include a methoxycarbonyl group, an ethoxycarbonyl group, a propoxycarbonyl group, and an isopropoxycarbonyl group. Of these, a methoxycarbonyl group is preferable.

That the "stereochemistry may be any of (S), (R) and (SR)" means it may be any of (S) form, (R) form, and a racemate which is a mixture of equivalent amounts of (S) form and (R) form.

X is preferably a covalent bond, an ethylene group or a vinylene group.

Y is preferably a divalent group represented by the formula

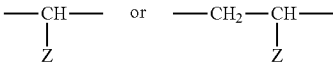

wherein Z is as described above, more preferably a divalent group represented by the formula

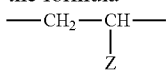

wherein Z is as described above, and still more preferably an ethylene group.

Preferably, $R_1$, $R_2$, $R_3$, $R_4$ and $R_5$ are each independently a hydrogen atom, a hydroxyl group or an alkoxy group having a carbon number of 1 to 3, or $R_1$ and $R_2$, or $R_2$ and $R_3$ in combination optionally form a methylenedioxy group.

At least one (preferably 1 to 3, more preferably 1 or 2) of $R_1$, $R_2$, $R_3$, $R_4$ and $R_5$ is preferably a hydroxyl group, and $R_3$ is more preferably a hydroxyl group. On the other hand, when X is a covalent bond, $R_1$ and $R_5$ are preferably hydroxyl groups.

Preferably, $R_6$ and $R_7$ are each independently a hydrogen atom, a hydroxyl group or an alkoxy group having a carbon number of 1 to 3. More preferably, $R_6$ is a hydrogen atom, a hydroxyl group or an alkoxy group having a carbon number of 1 to 3, and $R_7$ is a hydrogen atom. Still more preferably, $R_6$ is a hydroxyl group and $R_7$ is a hydrogen atom.

Preferably, $R_8$ and $R_9$ are each independently a hydrogen atom, a hydroxyl group or an alkoxy group having a carbon number of 1 to 3. More preferably, $R_8$ and $R_9$ are each independently a hydroxyl group or an alkoxy group having a carbon number of 1 to 3.

Preferable examples of the compound represented by the formula (I') include the compounds of Examples 1 to 36 to be mentioned below. In addition, preferable examples of the compound represented by the formula (I) include the compounds of Examples 1, 4, 5, 6 to 10, 14 to 23, and 25 to 36 to be mentioned below.

Examples of the salt of the compound represented by the formula (I), (I'), (IV), (V) or (VI) include salts with inorganic acids (e.g., hydrochloride, hydrobromide, sulfate, nitrate, phosphate, and the like); salts with organic acids (e.g., formate, acetate, trifluoroacetate, maleate, tartrate, citrate, fumarate, methanesulfonate, benzenesulfonate, p-toluenesulfonate, and the like); salts with acidic or basic amino acids (e.g., aspartic acid, glutamic acid, arginine, lysine, ornithine, and the like); salts with inorganic bases [for example, salts with metal (alkaline metal such as potassium, sodium, and the like; alkaline earth metal such as calcium, magnesium, and the like; aluminum), ammonium salt and the like]; and salts with organic bases (e.g., trimethylamine, triethylamine, pyridine, picoline, ethanolamine, diethanolamine, triethanolamine, dicyclohexylamine, N,N'-dibenzylethylenediamine, and the like). As the above-mentioned salt, pharmacologically acceptable salts are preferably used.

The compound of the present invention represented by the following formula (I) is obtained by reacting an amine component with a carboxylic acid component or an acid chloride thereof. In the following, a production method of a compound represented by the formula (I) (hereinafter to be also referred to as compound (I)) is explained.

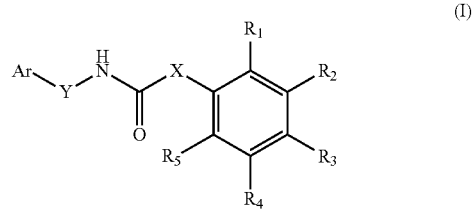

(I)

wherein $R_1$-$R_5$, Ar, X and Y are as described above.

Production Method of Compound (I).

A compound represented by the formula (I) can be produced by (i) subjecting amine component (VII) and carboxylic acid component (VIII) to a condensation reaction using a dehydrating-condensing agent, or (ii) once converting carboxylic acid component (VIII) to acid chloride (IX), and subjecting the compound and amine component (VII) to a condensation reaction in the presence of a base. In this case, compound (I) can be obtained by protecting a hydroxyl group and the like with a protecting group, and removing the protecting group after the condensation reaction, where necessary.

(VII)

wherein Ar and Y are as described above.

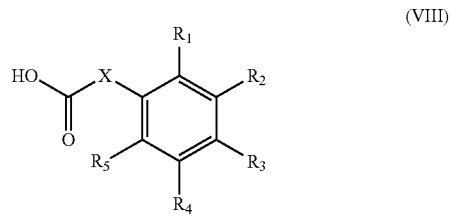

(VIII)

wherein $R_1$-$R_5$ and X are as described above.

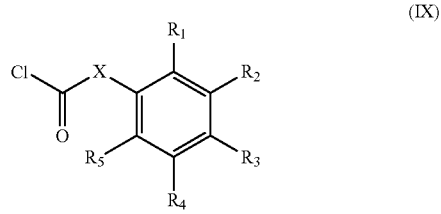

(IX)

wherein R₁-R₅ and X are as described above.

While a production method of (i) is explained in detail in the following, the method is not limited thereto.

Amine component (VII) may be a salt such as hydrochloride, p-toluenesulfonate and the like, and carboxylic acid component (VIII) may be a salt such as dicyclohexylamine salt and the like. When amine component (VII) is a salt, the reaction can be carried out by adding a base such as triethylamine and the like during the condensation reaction. While the ratio of amine component (VII) and carboxylic acid component (VIII) to be used is not limited, 0.8 to 1.2 equivalents of carboxylic acid component (VIII) may be used relative to 1 equivalent of amine component (VII) to achieve a reaction in a good yield.

The solvent to be used is not particularly limited as long as it does not react with amine component (VII) and carboxylic acid component (VIII) and, for example, dichloromethane (DCM), N,N-dimethylformamide (DMF), chloroform, dimethyl sulfoxide (DMSO), N-methylpyrrolidone (NMP), and a mixed solvent thereof can be used. Of these, dichloromethane and N,N-dimethylformamide are preferable. The amount of the solvent is 10- to 500-fold weight, preferably 15- to 100-fold weight, relative to amine component (VII).

As a dehydrating-condensing agent, a general condensing agent used for peptide synthesis and the like may be used and, for example, N,N'-dicyclohexylcarbodiimide (DCC), 1-ethyl-3-(3-dimethylaminopropyl)carbodiimide hydrochloride (EDCI.HCl), 2-(1H-benzotriazol-1-yl)-1,1,3,3-tetramethyluronium hexafluorophosphate (HBTU), and the like can be used. In this case, a condensation accelerator such as 1-hydroxybenzotriazole (HOBt) and the like may be used. The amount of the dehydrating-condensing agent to be used is 1.0 to 2.0 equivalents, preferably 1.05 to 1.20 equivalents, relative to amine component (VII). The amount of the condensation accelerator to be used is 0.5 to 3.0 equivalents, preferably 1.0 to 1.5 equivalents, relative to amine component (VII).

The reaction time is preferably about 3 to 24 hr, depending on the reaction temperature, which is preferably 5 to 35° C.

The obtained compound (I) can be isolated and purified according to a conventional method. For example, when compound (I) is purified by crystallization, ethyl acetate, ethanol, methanol, diethyl ether, chloroform, dichloromethane, n-hexane and a mixed solvent thereof can be used as a solvent. As a purification method by chromatography, preparative thin-layer chromatography (PTLC) or silica gel column chromatography can be used. As an eluent therefor, the solvents recited earlier as the crystallization solvent can be used.

Acid chloride (IX) to be used in the production method of (ii) can be obtained by reacting carboxylic acid component (VIII) with oxalyl chloride or thionyl chloride according to a conventional method. Acid chloride (IX) can be reacted with amine component (VII) in the presence of a base such as triethylamine, sodium hydroxide, and the like. While the ratio of amine component (VII) and acid chloride (IX) is not limited, 0.8 to 1.2 equivalents of acid chloride (IX) may be used relative to 1 equivalent of amine component (VII) to achieve a reaction in a good yield. The amount of the base to be used is 0.8 to 3.0 equivalents, preferably 1.0 to 1.5 equivalents, relative to amine component (VII). As the solvent to be used, those recited as the solvents to be used in the aforementioned production method of (i) can be used. The reaction time and the reaction temperature are the same as those in the production method of (i).

The thus-obtained compound of the present invention or a salt thereof can be provided as a whitening agent. The whitening agent of the present invention contains the compound of the present invention or a salt thereof, and can be added to whitening cosmetics singly or in combination with other whitening components. Other whitening components permitting combination with the whitening agent of the present invention are not particularly limited, and those having at least any of the tyrosinase activity inhibitory action, anti-inflammatory action, antioxidant action (including superoxide dismutase-like action), and excitometabolic action, which are said to be related to a whitening action, can be mentioned.

When the whitening agent of the present invention is added to whitening cosmetics, it can be used in combination with components generally used as starting materials for cosmetics, for example, flavor, preservative, chelate compound, polyol, plant extract (herbal medicine extract) and the like.

Other features of the invention will become apparent in the course of the following descriptions of exemplary embodiments which are given for illustration of the invention and are not intended to be limiting thereof.

EXAMPLES

In the following Production Examples, the structures of the synthesized compounds were identified by nuclear magnetic resonance spectrum (Bruker AVANCE 400).

Example 1

Serotonin hydrochloride (300 mg, 1.41 mmol) and trans-cinnamic acid (208 mg, 1.41 mmol) were dissolved in a mixed solvent of dichloromethane (6 ml) and N,N-dimethylformamide (6 ml), and the solution was maintained at 0° C. To this solution were added triethylamine (216 μl, 1.55 mmol), 1-hydroxybenzotriazole hydrate (HOBt H₂O, 237 mg, 1.55 mmol), and 1-ethyl-3-(3-dimethylaminopropyl)carbodiimide hydrochloride (EDCI HCl, 297 mg, 1.55 mmol), and the mixture was gradually warmed to room temperature and stirred at room temperature for 16 hours. The solvent was removed under reduced pressure, water (10 ml) was added to the residue, and the mixture was extracted twice with ethyl acetate (10 ml). The ethyl acetate layer was washed twice with 5% aqueous citric acid solution (5 ml), once with saturated brine (5 ml), twice with 5% aqueous sodium hydrogen carbonate solution (5 ml), and once with saturated brine (5 ml), and dried over anhydrous magnesium sulfate. Magnesium sulfate was removed by filtration, and the filtrate was concentrated under reduced pressure, and purified by preparative thin-layer chromatography (PTLC, eluent: ethyl acetate) to give N-[2-(5-hydroxy-1H-indol-3-yl)ethyl]-3-phenyl-2-propenamide (217 mg, yield 50.0%) as a viscous oil.

Example 4

Serotonin hydrochloride (300 mg, 1.41 mmol) and trans-2,4-dihydroxycinnamic acid (253 mg, 1.41 mmol) were dissolved in a mixed solvent of dichloromethane (6 ml) and N,N-dimethylformamide (6 ml), and the solution was maintained at 0° C. To this solution were added triethylamine (216 μl, 1.55 mmol), 1-hydroxybenzotriazole hydrate (HOBt H$_2$O, 237 mg, 1.55 mmol), and 1-ethyl-3-(3-dimethylaminopropyl)carbodiimide hydrochloride (EDCI HCl, 297 mg, 1.55 mmol), and the mixture was gradually warmed to room temperature and stirred at room temperature for 16 hours. The solvent was removed under reduced pressure, water (10 ml) was added to the residue, and the mixture was extracted twice with ethyl acetate (10 ml). The ethyl acetate layer was washed twice with 5% aqueous citric acid solution (5 ml), once with saturated brine (5 ml), twice with 5% aqueous sodium hydrogen carbonate solution (5 ml), and once with saturated brine (5 ml), and dried over anhydrous magnesium sulfate. Magnesium sulfate was removed by filtration, and the filtrate was concentrated under reduced pressure, and purified by preparative thin-layer chromatography (PTLC, eluent: ethyl acetate-n-hexane=2:1, 0.01% formic acid) to give N-[2-(5-hydroxy-1H-indol-3-yl)ethyl]-3-(2,4-dihydroxyphenyl)-2-propenamide (243 mg, yield 51.0%) as a viscous oil.

Example 17

3-Methyl-4-hydroxybenzaldehyde (794 mg, 5.83 mmol), malonic acid (911 mg, 8.75 mmol) and piperidine (144 μl) were added to pyridine (5 ml), and the mixture was stirred at 60° C. for 22 hours under an argon atmosphere. The reaction mixture was allowed to cool to room temperature, and water (20 ml) was added. 6N Hydrochloric acid was added to allow precipitation of a solid. The precipitated solid was collected by filtration, and the filtrate was washed with water and dried under reduced pressure. The obtained solid was recrystallized from diethylether-n-hexane to give 3-methyl-4-hydroxycinnamic acid (872 mg, yield 84.0%) as crystals.

$^1$H NMR (DMSO, 400 MHz) δ 9.95 (OH), 7.45 (d, J=15.9 Hz, 1H), 7.42 (s, 1H), 7.32 (d, J=8.3 Hz, 1H), 6.79 (d, J=8.3 Hz, 1H), 6.26 (d, J=15.9 Hz, 1H), 2.13 (s, 3H).

Serotonin hydrochloride (300 mg, 1.41 mmol) and 3-methyl-4-hydroxycinnamic acid (251 mg, 1.41 mmol) obtained above were dissolved in a mixed solvent of dichloromethane (10 ml) and N,N-dimethylformamide (5 ml), and the solution was maintained at 0° C. To this solution were added triethylamine (216 μl, 1.55 mmol), 1-hydroxybenzotriazole hydrate (HOBt H$_2$O, 237 mg, 1.55 mmol), and 1-ethyl-3-(3-dimethylaminopropyl)carbodiimide hydrochloride (EDCI HCl, 297 mg, 1.55 mmol), and the mixture was gradually warmed to room temperature and stirred at room temperature for 16 hours. The solvent was removed under reduced pressure, water (10 ml) was added to the residue, and the mixture was extracted twice with ethyl acetate (10 ml). The ethyl acetate layer was washed twice with 5% aqueous citric acid solution (5 ml), once with saturated brine (5 ml), twice with 5% aqueous sodium hydrogen carbonate solution (5 ml), and once with saturated brine (5 ml), and dried over anhydrous magnesium sulfate. Magnesium sulfate was removed by filtration, and the filtrate was concentrated under reduced pressure. The residue was recrystallized from ethyl acetate-ethanol-chloroform to give N-[2-(5-hydroxy-1H-indol-3-yl)ethyl]-3-(3-methyl-4-hydroxyphenyl)-2-propenamide (307 mg, yield 65.0%) as crystals.

Example 18

Methanol (5 ml) was maintained at 0° C., and thionyl chloride (2.4 ml) was added dropwise under an argon atmosphere. To this solution was added 5-hydroxy-L-tryptophan (2.0 g), and the mixture was gradually warmed from 0° C. to room temperature, and stirred at room temperature overnight. The reaction mixture was concentrated under reduced pressure, and the residue was crystallized from a mixed solvent of ethanol and ether to give 5-hydroxy-L-tryptophan methyl ester hydrochloride (1.8 g, yield 74%) as crystals.

As mentioned above, 5-hydroxy-L-tryptophan methyl ester hydrochloride (350 mg, 1.29 mmol) and ferulic acid (251 mg, 1.29 mmol) were dissolved in a mixed solvent of dichloromethane (6 ml) and N,N-dimethylformamide (6 ml), and the solution was maintained at 0° C. To this solution were added triethylamine (198 μl, 1.4 mmol), 1-hydroxybenzotriazole hydrate (HOBt H$_2$O, 217 mg, 1.4 mmol), and 1-ethyl-3-(3-dimethylaminopropyl)carbodiimide (EDCI HCl, 217 mg, 1.4 mmol), the solution temperature was gradually raised from 0° C., and the mixture was stirred at room temperature for 16 hours. The solvent was removed under reduced pressure, water (20 ml) was added to the residue, and the mixture was extracted twice with ethyl acetate (20 ml). The ethyl acetate layer was washed twice with 5% aqueous citric acid solution (5 ml), once with saturated brine (5 ml), twice with 5% aqueous sodium hydrogen carbonate solution (5 ml), and once with saturated brine (5 ml), and dried over anhydrous magnesium sulfate. Magnesium sulfate was removed by filtration, and the filtrate was concentrated under reduced pressure, and purified by silica gel column chromatography (eluent: chloroform:methanol=3:1) to give 3-(3-methoxy-4-hydroxyphenyl)-N-[2-(5-hydroxy-1H-indol-3-yl)-1-methoxycarbonylethyl]-2-propenamide (413 mg, yield 78.0%) as a powder.

Example 20

3-(3-Methoxy-4-hydroxyphenyl)-N-[2-(5-hydroxy-1H-indol-3-yl)-1-methoxycarbonylethyl]-2-propenamide synthesized from 5-hydroxy-L-tryptophan methyl ester hydrochloride (704 mg, 2.6 mmol) in the same manner as in Example 18 was dissolved in a mixed solvent of water (11.8 ml), 2.5N NaOH aqueous solution (11.8 ml), and N,N-dimethylformamide (23.6 ml) without purification, and the mixture was stirred at room temperature overnight. The reaction solvent was concentrated under reduced pressure, cooled to 0° C., and adjusted with 6N aqueous HCl solution to pH 1 to 2. The solution was extracted three times with ethyl acetate (30 ml), and the organic layer was washed with 3N HCl (20 ml) and dried over anhydrous magnesium sulfate. Magnesium sulfate was removed by filtration, and the filtrate was concentrated under reduced pressure, and purified by preparative thin-layer chromatography (PTLC, eluent: chloroform:methanol=3:1) to give 3-(3-methoxy-4-hydroxyphenyl)-N-[2-(5-hydroxy-1H-indol-3-yl)-1-hydroxycarbonylethyl]-2-propenamide (147 mg, yield 15.4%) as a powder.

Example 35

Serotonin hydrochloride (430 mg, 2 mmol) and 2,6-dihydroxybenzoic acid (312 mg, 2 mmol) were dissolved in N,N-dimethylformamide (25 ml), and the solution temperature was maintained at 0° C. To this solution were added triethylamine (310 μl, 2.1 mmol), 1-hydroxybenzotriazole hydrate (HOBt H$_2$O, 346 mg, 2.1 mmol), and 1-ethyl-3-(3-dimethylaminopropyl)carbodiimide (EDCI HCl, 429 mg, 2.1 mmol), the solution temperature was gradually warmed from 0° C. to room temperature, and the mixture was stirred at room temperature for 16 hours. The solvent was removed under reduced pressure, water (20 ml) was added to the residue, and the mixture was extracted twice with ethyl acetate (20 ml).

The ethyl acetate layer was washed twice with 5% aqueous citric acid solution (5 ml), once with saturated brine (5 ml), twice with 5% aqueous sodium hydrogen carbonate solution (5 ml), and once with saturated brine (5 ml), and dried over anhydrous magnesium sulfate. Magnesium sulfate was removed by filtration, and the filtrate was concentrated under reduced pressure, purified by preparative thin-layer chromatography (PTLC, eluent: ethyl acetate:hexane=3:1) to give 2,6-dihydroxy-N-[2-(5-hydroxy-1H-indol-3-yl)ethyl]-benzamide (93 mg, yield 14.9%) as a powder.

The compounds of other Examples, which are shown in the following Table 1, were also synthesized in the same manner as in Examples 1, 4, 17, 18, 20 and 35. In addition, compounds having a carboxyl group were obtained by alkaline hydrolysis of the ester bond of the corresponding methoxycarbonyl group. The compounds of Reference Examples 1 and 2, which are shown in the following Table 1, were also synthesized in the same manner as in Examples 1, 4, 17, 18, 20 and 35.

TABLE 1

| Prod. Ex. | structural formula | property, yield |
|---|---|---|
| Ex. 1 | | $^1$H NMR (DMSO, 400 MHz) δ 10.49 (NH), 8.59 (OH), 8.20 (NH), 7.56 (d, J = 6.9, 2H), 7.4 (m, 4H), 7.12 (d, J = 8.6 Hz, 1H), 7.06 (d, J = 2.1 Hz, 1H), 6.85 (d, J = 2.1 Hz, 1H), 6.64 (d, J = 15.8 Hz, 1H), 6.59 (dd, J = 8.6, 2.2 Hz, 1H), 3.44 (m, 2H), 7.42 (t, J = 7.4 Hz, 2H). ESI-MS: [M − H]$^-$ = 305.0. yield: 50.0%. |
| Ex. 2 | | $^1$H NMR (DMSO, 400 MHz) δ 10.48 (NH), 8.11 (NH), 7.50 (d, J = 8.8 Hz, 2H) 7.36 (d, J = 15.7 Hz, 1H), 7.12 (d, J = 8.8 Hz, 1H), 7.06 (s, 1H), 6.97 (d, J = 8.8 Hz, 1H), 6.85 (d, J = 2.3 Hz, 1H), 6.60 (dd, J = 2.3, 8.8 Hz, 1H), 6.48 (d, J = 2.3 Hz, 1H), 3.79 (s, 3H), 3.43 (m, 2H), 2.79 (t, J = 7.6 Hz, 2H). ESI-MS: [M − H]$^-$ = 335.3. yield: 88.0%. |
| Ex. 3 | | $^1$H NMR (DMSO, 400 MHz) δ 10.50 (NH), 8.12 (NH), 7.24 (d, J = 15.6 Hz, 1H), 7.13 (d, J = 8.8 Hz, 1H), 7.05 (s, 1H), 6.94 (s, 1H), 6.85 (s, 1H), 6.83 (d, J = 8 Hz, 1H), 6.74 (d, J = 8 Hz, 1H), 6.59 (dd, J = 2.3, 8.8 Hz, 1H), 6.33 (d, J = 15.6 Hz, 1H), 3.30 (s, 3H), 3.25 (m, 2H), 2.78 (t, J = 7.6 Hz, 2H). ESI-MS: [M − H]$^-$ = 351.2. yield: 27.0%. |
| Ex. 4 | | $^1$H NMR (DMSO, 400 MHz) δ 10.48 (NH), 9.88 (OH), 9.65 (OH), 8.58 (OH), 8.00 (NH), 7.54 (d, J = 15.8 Hz, 1H), 7.22 (d, J = 8.6 Hz, 1H), 7.12 (d, J = 8.6 Hz, 1H), 7.05 (d, J = 2.3 Hz, 1H), 6.85 (d, J = 2.3 Hz, 1H), 6.59 (dd, J = 2.3, 8.6 Hz, 1H), 6.45 (d, J = 15.8 Hz, 1H), 6.34 (d, J = 2.3 Hz, 1H), 6.25 (dd, J = 2.3, 6.8 Hz, 1H), 3.43 (m, 2H), 2.78 (t, J = 7.4 Hz, 2H). ESI-MS: [M − H]$^-$ = 351.2. yield: 51.0%. |
| Ex. 5 | | $^1$H NMR (DMSO, 400 MHz) δ 10.48 (d, J = 2.1 Hz, 1H, NH), 8.59 (OH), 8.07 (NH), 7.34 (d, J = 15.7 Hz, 1H), 7.14 (d, J = 1.6 Hz, 1H), 7.12 (d, J = 8.7 Hz, 1H), 7.07 (m, 2H) [7.07 (dd, J = 8.0, 1.6 Hz, 1H), 7.05 (s, 1H)], 6.94 (d, J = 8.0 Hz, 1H), 6.84 (d, J = 2.3 Hz, 1H), 6.59 (dd, J = 8.6, 2.3 Hz, 1H), 6.47 (d, J = 15.7 Hz, 1H), 6.07 (s, 2H), 3.43 (m, 2H), 2.77 (t, J = 7.4 Hz, 2H). ESI MS: [M − H]$^-$ = 337.3. (methylene moiety was dissociated, observed as 3.4-OH.) yield: 68.0%. |

TABLE 1-continued

| Prod. Ex. | structural formula | property, yield |
|---|---|---|
| Ref. Ex. 1 | (structure) | $^1$H NMR (DMSO, 400 MHz) δ 10.48 (NH), 8.07 (NH, amide), 7.24 (d, J = 15.6 Hz, 1H), 7.12 (d, J = 8.6 Hz, 1H), 7.05 (s, 1H), 6.94 (d, J = 2.0 Hz, 1H), 6.84 (d, J = 2.0 Hz, 1H), 6.82 (d, J = 2.0 Hz, 1H), 6.74 (d, J = 8.1 Hz, 1H), 6.59 (dd, J = 8.6, 2.3 Hz, 1H), 6.33 (d, J = 15.6 Hz, 1H), 3.44 (m, 2H), 2.78 (m, 2H). ESI-MS: [M + H]$^+$ = 339.1, [M + Na]$^+$ = 361.0, [M − H]$^−$ = 337.2, [2M − H]$^−$ = 675.2. yield: 54.0%. |
| Ex. 6 | (structure) | $^1$H NMR (DMSO, 400 MHz) δ 10.46 (NH), 9.00 (OH), 8.61 (OH), 7.88 (t, J = 5.6 Hz, 1H, NH), 7.11 (d, J = 8.6 Hz, 1H), 7.00 (d, J = 2.3 Hz, 1H), 6.98 (m, 2H), 6.82 (d, J = 2.3 Hz, 1H), 6.65 (m, 1H), 6.58 (dd, J = 8.6, 2.3 Hz, 1H), 3.25 (m, 2H), 2.69 (m, 4H), 2.32 (m, 2H). ESI-MS: [M + H]$^+$ = 325.1, [M + Na]$^+$ = 347.2, [M − H]$^−$ = 323.2, yield: 63.0%. |
| Ex. 7 | (structure) | $^1$H NMR (DMSO, 400 MHz) δ 10.46 (NH), 8.59 (OH, 2H), 7.89 (NH), 7.11 (d, J = 8.6 Hz, 1H), 7.01 (d, J = 2.3 Hz, 1H), 6.82 (d, J = 2.3 Hz, 1H), 6.76 (d, J = 1.9 Hz, 1H), 6.65 (d, J = 8.0 Hz, 1H), 6.58 (dd, J = 8.6, 2.3 Hz, 1H), 6.57 (dd, J = 8.0, 2.3 Hz, 1H), 3.74 (s, 3H), 3.28 (m, 2H), 2.32 (m, 2H), 2.69 (m, 4H). ESI-MS: [M + Na]$^+$ = 377.1, [M − H]$^−$ = 353.3. yield: 80.0%. |
| Ex. 8 | (structure) | $^1$H NMR, (DMSO, 400 MHz) δ 10.48 (NH), 8.76 (OH), 8.59 (OH), 8.02 (NH), 7.34 (d, J = 15.6 Hz, 1H), 7.12 (d, J = 8.6 Hz, 1H), 7.06 (d, J = 2.3 Hz, 1H), 6.85 (s, 3H), 6.59 (dd, J = 8.6, 2.3 Hz, 1H), 6.48 (d, J = 15.6 Hz, 1H), 3.80 (s, 3H), 3.43 (td, J = 7.4, 7.4 Hz, 2H), 3.32 (s, 3H), 2.78 (t, J = 7.4 Hz, 2H). ESI-MS: [M + Na]$^+$ = 405.1, [M − H]$^−$ = 381.2. yield: 77.0%. |
| Ex. 9 | (structure) | $^1$H NMR, (DMSO, 400 MHz) δ 10.47 (NH), 8.74 (OH), 8.57 (OH), 7.97 (NH), 7.11 (d, J = 8.6 Hz, 1H), 7.00 (d, J = 2.2 Hz, 1H), 6.82 (m, 2H), 6.68 (d, J = 8 Hz, 1H), 6.62 (dd, J = 8, 1.8 Hz, 1H), 6.58 (dd, J = 8.6, 2.2 Hz, 1H), 3.73 (s, 3H), 3.28 (m, 4H), 2.71 (t, J = 7.4 Hz, 2H). ESI-MS: [M + H]$^+$ = 341.2, [M + Na]$^+$ = 363.1, [2M − H]$^−$ = 339.2, [2M − H]$^−$ = 679.3. yield: 56.0%. |
| Ex. 10 | (structure) | $^1$H NMR (DMSO, 400 MHz) δ 10.64 (NH), 9.41 (OH), 8.05 (NH), 7.34 (d, J = 15.7 Hz, 1H), 7.22 (d, J = 8.7 Hz, 1H), 7.13 (m, 2H), 7.05 (d, J = 2.3 Hz, 1H), 7.00 (dd, J = 1.8, 2.3 Hz, 1H), 6.79 (d, J = 8.1 Hz, 1H), 6.71 (dd, J = 2.4, 8.2 Hz, 1H), 6.46 (d, J = 15.7 Hz, 1H), 3.81 (s, 3H), 3.76 (s, 3H), 3.46 (m, 2H), 2.85 (t, J = 7.2 Hz, 2H). ESI-MS: [M + Na]$^+$ = 389.2, [M − H]$^−$ = 365.2. yield: 80.0%. |

TABLE 1-continued

| Prod. Ex. | structural formula | property, yield |
|---|---|---|
| Ex. 11 | (structure: 5-hydroxytryptamine coupled with 4-hydroxy-3-methoxy... p-coumaroyl derivative) | ¹H NMR (DMSO, 400 MHz) δ 10.46 (1H), 8.07 (1H), 7.38 (d, J = 8.6 Hz, 2H), 7.32 (d, J = 15.7 Hz, 2H), 7.22 (d, J = 8.7 Hz, 1H), 7.11 (d, J = 2.4 Hz, 1H), 7.04 (d, J = 2.4 Hz, 1H), 6.78 (d, J = 8.6 Hz, 2H), 6.71 (dd, J = 8.7, 2.4 Hz, 2H), 6.40 (d, J = 15.7 Hz, 2H), 3.75 (s, 3H), 3.43 (m, 2H), 2.84 (t J = 7.3 Hz, 2H). ESI-MS: [M + Na]⁺ = 359.2, [M − H]⁻ = 335.3, [2M − H]⁻ = 671.4. yield: 90.0%. |
| Ex. 12 | (structure) | ¹H NMR (DMSO, 400 MHz) δ 10.81 (1H), 8.05 (1H), 7.55 (d, J = 7.9 Hz, 1H), 7.34 (d, J = 7.9 Hz, 1H), 7.33 (d, J = 15.8 Hz, 1H), 7.17 (d, J = 2.3 Hz, 1H), 7.11 (d, J = 1.9 Hz, 1H), 7.08 (m, 1H), 7.00 (m, 2H), 6.78 (d, J = 8.1 Hz, 1H), 6.43 (d, J = 15.7 Hz, 1H), 3.82 (s, 3H), 3.45 (m, 2H), 2.87 (t, J = 7.4 Hz, 2H). ESI-MS: [M + Na]⁺ = 359.2, [M − H]⁻ = 335.3. yield: 64.0%. |
| Ex. 13 | (structure) | ¹H NMR (DMSO, 400 MHz) δ 10.81 (NH), 9.82 (OH), 8.01 (NH), 7.55 (d, J = 7.8 Hz, 1H), 7.38 (d, J = 8.6 Hz, 2H), 7.33 (d, J = 15.7 Hz, 1H), 7.34 (d, J = 7.1 Hz, 1H), 7.16 (d, J = 2.2 Hz, 1H), 7.06 (t, J = 7.1 Hz, 1H), 6.98 (t, J = 7.1 Hz, 1H), 6.79 (d, J = 8.6 Hz, 1H), 6.41 (d, J = 15.7 Hz, 1H), 3.45 (m, 2H), 2.88 (t, J = 7.3 Hz, 2H). ESI-MS: [M + Na]⁺ = 329.2, [M − H]⁻ = 305.2, [2M − H]⁻ = 611.3. yield: 73.0%. |
| Ex. 14 | (structure) | ¹H NMR (DMSO, 400 MHz) δ 10.48 (NH), 9.32 (NH), 8.58 (OH), 8.02 (OH), 7.30 (d, J = 15.7 Hz, 1H), 7.12 (d, J = 8.6 Hz, 1H), 7.10 (d, J = 1.8 Hz, 1H), 7.06 (d, J = 2.2 Hz, 1H), 6.98 (dd, J = 1.8, 8.2 Hz, 1H), 6.85 (d, J = 2.2 Hz, 1H), 6.80 (d, J = 8.2 Hz, 1H), 6.59 (dd, J = 8.6, 2.2 Hz, 1H), 6.43 (d, J = 15.7 Hz, 1H), 4.05 (q, J = 7.0 Hz, 2H), 3.43 (m, 1H), 2.78 (m, 1H), 1.35 (t, J = 7.0 Hz, 3H). ESI-MS: [M + Na]⁺ = 389.2, [M − H]⁻ = 365.2. yield: 79.0%. |
| Ex. 15 | (structure) | ¹H NMR (DMSO, 400 MHz) δ 10.5 (NH), 8.08 (NH), 7.15 (d, J = 15.6 Hz, 1H), 7.12 (d, J = 8.5 Hz, 1H), 7.05 (s, 1H), 6.85 (d, J = 2.1 Hz, 1H), 6.59 (dd, J = 2.3, 8.5 Hz, 1H), 6.48 (s, 2H), 6.28 (d, J = 15.6 Hz, 1H), 3.35 (m, 2H), 2.77 (m, 2H). ESI-MS: [M − H]⁻ = 353.3. yield: 43.0%. |
| Ex. 16 | (structure) | ¹H NMR (DMSO, 400 MHz) δ 10.49 (NH), 9.39 (OH, 2H), 8.65 (OH), 8.19 (NH), 7.21 (d, J = 15.7 Hz, 1H), 7.12 (d, J = 8.7 Hz, 1H), 7.05 (d, J = 2.3 Hz, 1H), 6.85 (d, J = 2.3 Hz, 1H), 6.60 (dd, J = 2.3, 8.7 Hz, 1H), 6.45 (d, J = 15.7 Hz, 1H), 6.38 (d, J = 2.1 Hz, 2H), 6.23 (t, J = 2.12 Hz, 1H), 3.43 (m, 2H), 2.78 (t, J = 7.5 Hz, 2H). ESI-MS: [M − H]⁻ = 337.2. yield: 72.0%. |

TABLE 1-continued

| Prod. Ex. | structural formula | property, yield |
|---|---|---|
| Ex. 17 | (structure: 5-hydroxytryptamine linked via amide to trans-cinnamoyl group with 3-methyl-4-hydroxyphenyl) | $^1$H NMR (DMSO, 400 MHz) δ 10.48 (NH), 8.61 (OH), 8.02 (NH), 7.29 (d, J = 15.7 Hz, 1H), 7.27 (s, 1H), 7.20 (dd, J = 2.0, 8.3 Hz, 1H), 7.12 (d, J = 8.6 Hz, 1H), 7.05 (d, J = 2.3 Hz, 1H), 6.85 (d, J = 2.2 Hz, 1H), 6.79 (d, J = 8.3 Hz, 1H), 6.59 (dd, J = 2.3, 8.6 Hz, 1H), 6.40 (d, J = 15.7 Hz, 1H), 3.43 (m, 2H), 2.75 (t, J = 7.6 Hz, 2H). ESI-MS: [M − H]$^-$ = 335.0. yield: 65.0%. |
| Ex. 18 | (structure with CO$_2$CH$_3$ and 3-methoxy-4-hydroxyphenyl cinnamoyl) | $^1$H NMR (DMSO, 400 MHz) δ 10.54, 9.48, 8.62, 8.30 (NH, OH, 4H), 7.29 (d, J = 15.6 Hz, 1H), 7.12 (d, J = 8.12, 1H), 7.11 (s, 1H), 7.06 (d, J = 2.4 Hz, 1H), 6.98 (d, J = 8.16 Hz, 1H), 6.81 (d, J = 2.2 Hz, 1H), 6.78 (d, J = 8.12 Hz, 1H), 6.58 (dd, J = 2.2, 8.16 Hz, 1H), 6.53 (d, J = 15.6 Hz, 1H), 4.16 (m, 1H), 3.81 (s, 3H), 3.62 (s, 3H), 3.05 (m, 1H). ESI-MS: [M + Na]$^+$ = 433.3, [M − H]$^-$ = 409.2. yield: 78.0%. |
| Ex. 19 | (structure with CO$_2$CH$_3$ and 4-hydroxyphenyl cinnamoyl) | $^1$H NMR (DMSO, 400 MHz) δ 10.54 (s, NH), 9.8 (brs, OH), 8.62 (brs, OH), 8.34 (d, J = 7.5 Hz, NH), 7.38 (d, J = 8.6 Hz, 2H), 7.30 (d, J = 15.7 Hz, 1H), 7.12 (d, J = 8.6 Hz, 1H), 7.05 (d, J = 2.4 Hz, 1H), 6.81 (d, J = 2.4 Hz, 1H), 6.78 (d, J = 8.6 Hz, 2H), 6.59 (dd, J = 2.3, 8.6 Hz, 1H), 6.48 (d, J = 15.7 Hz, 1H), 4.60 (m, 1H), 3.62 (s, 3H), 3.00 (m, 2H). ESI-MS: [M − H]$^-$ = 379.2. yield: 74.0%. |
| Ex. 20 | (structure with CO$_2$H and 3-methoxy-4-hydroxyphenyl cinnamoyl) | $^1$H NMR (DMSO, 400 MHz) δ 10.51 (NH), 9.44 (OH), 8.63 (OH), 8.17 (NH), 7.29 (d, J = 15.7 Hz, 1H), 7.12 (d, J = 8.6 Hz, 1H), 7.11 (d, J = 1.9 Hz, 1H), 7.06 (d, J = 2.3 Hz, 1H), 6.98 (dd, J = 8.2, 1.9 Hz, 2H), 6.87 (d, J = 2.2 Hz, 1H), 6.79 (d, J = 8.2 Hz, 1H), 6.59 (dd, J = 8.6, 2.3 Hz, 1H), 6.55 (d, J = 15.7 Hz, 1H), 4.58 (m, 1H), 3.00 (m, 2H). ESI-MS: [M + H]$^+$ = 397.0, [M − H]$^-$ = 395.0. yield: 15.0%. |
| Ex. 21 | (structure with CO$_2$H and 4-hydroxyphenyl cinnamoyl) | $^1$H NMR (DMSO, 400 MHz) δ 10.50 (NH), 9.83 (OH), 8.60 (OH), 8.17 (NH), 7.37 (d, J = 8.7 Hz, 2H), 7.28 (d, J = 15.7 Hz, 1H), 7.11 (d, J = 8.6 Hz, 1H), 7.04 (d, J = 2.2 Hz, 1H), 6.86 (d, J = 2.2 Hz, 1H), 6.78 (d, J = 8.7 Hz, 2H), 6.58 (dd, J = 8.7, 2.2 Hz, 1H), 6.50 (d, J = 15.7 Hz, 1H), 4.55 (m, 1H), 2.99 (m, 2H). ESI-MS: [M − H]$^-$ = 365.0. yield: 22.0%. |
| Ex. 22 | (structure: 5-hydroxytryptamine linked via amide to 2,3,4-trihydroxyphenyl cinnamoyl) | $^1$H NMR (DMSO, 400 MHz) δ 7.91, 7.87 (d, 1H), 7.79, 7.76 (d, 1H), 7.19-6.36 (m, 6H), 3.60, 3.58, 3.56 (t, 2H), 2.96, 2.94, 2.92 (t, 2H). ESI-MS: [M − H]$^-$ = 353.0. yield: 8.7%. |

TABLE 1-continued

| Prod. Ex. | structural formula | property, yield |
|---|---|---|
| Ex. 23 | (5-hydroxytryptamine coupled with 2,5-dihydroxycinnamamide) | $^1$H NMR (MeOH-d, 400 MHz) δ 7.84, 7.80 (d, J = 16 Hz, 1H), 7.19, 7.17 (d, J = 9 Hz 1H), 7.05 (s, 1H), 6.98 (s, 1H), 6.91 (s, 1H), 6.69 (s, 2H), 6.65, 6.61 (d, J = 16 Hz, 1H), 3.59 (t, 1H), 2.95 (t, 1H). ESI-MS: [M + H]$^+$ = 339.2, [M − H]$^−$ = 337.8. yield: 18.3%. |
| Ex. 24 | (4-methoxyphenethylamine coupled with 4-hydroxycinnamamide) | $^1$H NMR (DMSO, 400 MHz) δ 9.83 (s, 1H), 8.04, 8.02, 8.01 (t, 1H), 7.39, 7.37 (d, 2H), 7.33, 7.29 (d, 1H), 7.15, 7.13 (d, 2H), 6.87, 6.85 (d, 2H), 6.80, 6.78 (d, 2H), 6.41, 6.37 (d, 1H), 3.72 (s, 3H), 2.72, 2.70, 2.68 (2H, t). ESI-MS [M + H]$^+$ = 298.2, [M − H]$^−$ = 296.0. yield: 82.4%. |
| Ex. 25 | (3,4-dimethoxyphenethylamine coupled with 4-hydroxycinnamamide) | $^1$H NMR (DMSO, 400 MHz) δ 9.83 (s, 1H), 8.03, 8.01, 8.00 (t, 1H), 7.39, 7.37 (d, 2H), 7.34, 7.30 (d, 1H), 6.87, 6.85 (d, 1H), 6.83, 6.82 (d, 1H), 6.80, 6.78 (d, 2H), 6.74, 6.72 (d, 1H), 6.42, 6.39 (d, 1H), 3.74 (s, 3H), 3.71 (s, 3H), 2.72, 2.70, 2.68 (t, 2H). ESI-MS: [M + H]$^+$ = 328.2, [M − H]$^−$ = 325.9. yield: 82.1%. |
| Ex. 26 | (3-methoxy-4-hydroxyphenethylamine coupled with 4-hydroxycinnamamide) | $^1$H NMR (DMSO, 400 MHz) δ 9.82 (s, 1H), 8.70 (s, 1H), 8.01, 8.00, 7.98 (t, 1H), 7.39, 7.37 (d, 2H), 7.33, 7.29 (d, 1H), 6.80, 6.78 (d, 3H), 6.69, 6.67 (d, 1H), 6.61, 6.59 (d, 1H), 6.43, 6.39 (d, 1H), 3.75 (s, 3H), 2.68, 2.66, 2.64 (t, 2H). ESI-MS: [M + H]$^+$ = 314.0, [M − H]$^−$ = 312.0. yield: 85.9%. |
| Ex. 27 | (4-methoxybenzylamine coupled with 4-hydroxycinnamamide) | $^1$H NMR (DMSO, 400 MHz) δ 9.81 (s, 1H), 9.17 (s, 1H), 8.02, 8.00, 7.99 (t, 1H), 7.39, 7.37 (d, 2H), 7.33, 7.29 (d, 1H), 7.02, 7.00 (d, 2H), 6.80, 6.76 (d, 2H), 6.69, 6.67 (d, 2H), 6.41, 6.37 (d, 1H), 2.66, 2.64, 2.62 (t, 2H). ESI-MS: [M + H]$^+$ = 284.0, [M − H]$^−$ = 282.1. yield: 83.1%. |
| Ex. 28 | (3,4-dihydroxy/methoxybenzylamine coupled with 4-hydroxycinnamamide) | $^1$H NMR (DMSO, 400 MHz) δ 9.82 (s, 1H), 8.84 (s, 1H), 8.35, 8.34, 8.33 (t, 1H), 7.40, 7.38 (d, 2H), 6.86 (s, 1H), 6.80, 6.78 (d, 2H), 6.71 (s, 1H), 6.69 (s, 1H), 6.48, 6.44 (d, 1H), 4.28, 4.26 (d, 2H), 3.75 (s, 3H). ESI-MS: [M + H]$^+$ = 300.0, [M − H]$^−$ = 298.0. yield: 61.7%. |
| Ex. 29 | (3-hydroxy-4-methoxybenzylamine coupled with 4-hydroxycinnamamide) | $^1$H NMR (DMSO, 400 MHz) δ 9.83 (s, 1H), 8.92 (s, 1H), 8.37, 8.36, 8.34 (t, 1H), 7.40, 7.38 (d, 2H), 6.86, 6.84 (d, 1H), 6.80, 6.78 (d, 2H), 6.72 (s, 1H), 6.67, 6.65 (d, 1H), 6.48, 6.44 (d, 1H), 4.24, 4.23 (d, 2H), 3.73 (s, 3H). ESI-MS: [M + H]$^+$ = 300.0, [M − H]$^−$ = 298.3. yield: 81.8%. |

TABLE 1-continued

| Prod. Ex. | structural formula | property, yield |
|---|---|---|
| Ex. 30 | | $^1$H NMR (DMSO, 400 MHz) δ 10.80 (s, 1H), 9.88 (s, 1H), 9.65 (s, 1H), 8.03, 8.02, 8.00 (t, 1H), 7.57 (s, 1H), 7.55, 7.53 (d, 1H), 7.35, 7.33 (d, 1H), 7.24, 7.22 (d, 1H), 7.16, 7.15 (d, 1H), 7.09-7.05 (m, 1H), 7.00-6.96 (m, 1H), 6.47, 6.43 (d, 1H), 6.35 (s, 1H), 6.27, 6.25 (d, 1H), 3.47, 3.46, 3.44, 3.42 (q, 2H), 2.89, 2.87, 2.85 (t, 2H). ESI-MS: [M + H]$^+$ = 323.2, [M − H]$^−$ = 320.9. yield: 12.7%. |
| Ex. 31 | | $^1$H NMR (DMSO, 400 MHz) δ 10.81 (s, 1H), 9.73 (s, 1H), 8.06, 8.05, 8.04 (t, 1H), 7.57, 7.55 (d, 1H), 7.33, 7.32 (d, 2H), 7.28 (s, 1H), 7.21, 7.19 (d, 1H), 7.17, 7.16 (d, 1H), 7.09, 7.07, 7.05 (t, 1H), 7.00, 6.98, 6.96 (t, 1H), 6.92, 6.88 (d, 1H), 6.42, 6.38 (d, 1H), 3.48, 3.47, 3.45, 3.43 (q, 2H), 2.89, 2.88, 2.86 (t, 2H). ESI-MS: [M + H]$^+$ = 321.2, [M − H]$^−$ = 319.0 yield: 47.5%. |
| Ex. 32 | | $^1$H NMR (DMSO, 400 MHz) δ 10.51 (s, 1H), 9.14 (s, 1H), 8.94, 8.93, 8.92 (t, 1H), 8.61 (s, 1H), 7.30, 7.28 (d, 1H), 7.14, 7.12 (d, 1H), 7.08 (s, 1H), 6.92 (s, 1H), 6.90, 6.89 (d, 1H), 6.71, 6.69, 6.68 (t, 1H), 6.61, 6.59 (d, 1H), 3.55, 3.54, 3.52, 3.50 (q, 2H), 2.89, 2.87, 2.85 (t, 2H). ESI-MS: [M + H]$^+$ = 313.1, [M − H]$^−$ = 310.9. yield: 23.0%. |
| Ex. 33 | | $^1$H NMR (DMSO, 400 MHz) δ 10.50 (s, 1H), 10.06 (s, 1H), 8.69, 8.68, 8.66 (t, 1H), 8.62 (s, 1H), 7.69, 7.67 (d, 1H), 7.14, 7.12 (d, 1H), 7.07 (s, 1H), 6.88 (s, 1H), 6.61, 6.59 (d, 1H), 6.30, 6.27 (d, 1H), 6.23 (d, 1H), 3.53, 3.51, 3.49, 3.47 (q, 2H), 2.87, 2.85, 2.83 (t, 2H). ESI-MS: [M + H]$^+$ = 313.1, [M − H]$^−$ = 310.9. yield: 34.3%. |
| Ex. 34 | | $^1$H NMR (DMSO, 400 MHz) δ 10.51 (s, 1H), 9.00 (s, 1H), 8.82 (s, 1H), 8.62 (s, 1H), 7.24, 7.23 (d, 1H), 7.13, 7.12 (d, 1H), 7.08, 7.07 (d, 1H), 6.86, 6.84 (d, 1H), 6.74, 6.71 (d, 1H), 6.61, 6.59 (d, 1H), 3.55, 3.53, 3.51, 3.50 (q, 2H), 2.87, 2.86, 2.84 (t, 2H). ESI-MS: [M + H]$^+$ = 313.1, [M − H]$^−$ = 310.8. yield: 30.1%. |
| Ex. 35 | | $^1$H NMR (DMSO, 400 MHz) δ 10.54 (s, 1H), 9.01 (s, 1H), 8.62 (s, 1H), 7.16 (s, 1H), 7.14, 7.12 (d, 1H), 7.10, 7.09 (d, 1H), 6.90 (s, 1H), 6.62, 6.59 (d, 1H), 6.35, 6.33 (d, 2H), 3.64, 3.62, 3.61, 3.59 (q, 2H), 2.90, 2.88, 2.87 (t, 2H). ESI-MS: [M + H]$^+$ = 313.1, [M − H]$^−$ = 310.9. yield: 14.9%. |

TABLE 1-continued

| Prod. Ex. | structural formula | property, yield |
|---|---|---|
| Ref. Ex. 2 | (structure: 5-hydroxyindole-ethyl-NH-C(=O)-3,4-dihydroxyphenyl) | $^1$H NMR (DMSO, 400 MHz) δ 10.47 (s, 1H), 9.43 (s, 1H), 9.09 (s, 1H), 8.61 (s, 1H), 8.27, 8.25, 8.24 (t, 1H), 7.29 (s, 1H), 7.20, 7.18 (d, 1H), 7.13, 7.11 (s, 1H), 7.05 (s, 1H), 6.88 (s, 1H), 6.76, 6.74 (d, 1H), 6.60, 6.58 (d, 1H), 3.48, 3.46, 3.44, 3.42 (q, 2H), 2.83, 2.81, 2.79 (t, 2H). ESI-MS: [M + H]$^+$ = 313.1, [M − H]$^-$ = 310.9. yield: 32.6%. |
| Ex. 36 | (structure: 5-hydroxyindole-ethyl-NH-C(=O)-3,5-dihydroxyphenyl) | $^1$H NMR (DMSO, 400 MHz) δ 10.48 (s, 1H), 9.44, 9.43 (s, 1H), 8.60 (s, 1H), 8.36, 8.35, 3.34 (t, 1H), 7.13, 7.11 (d, 1H), 7.05 (s, 1H), 6.87 (b, 1H), 6.68 (s, 2H), 6.60, 6.58 (d, 1H), 6.35 (s, 1H), 3.47, 3.45, 3.43, 3.42 (q, 2H), 2.82, 2.81, 2.79 (t, 2H). ESI-MS: [M + H]$^+$ = 313.1, [M − H]$^-$ = 310.8. yield: 60.5%. |

Experimental Example 1

Melanin Production Suppression Test

Figure 2:
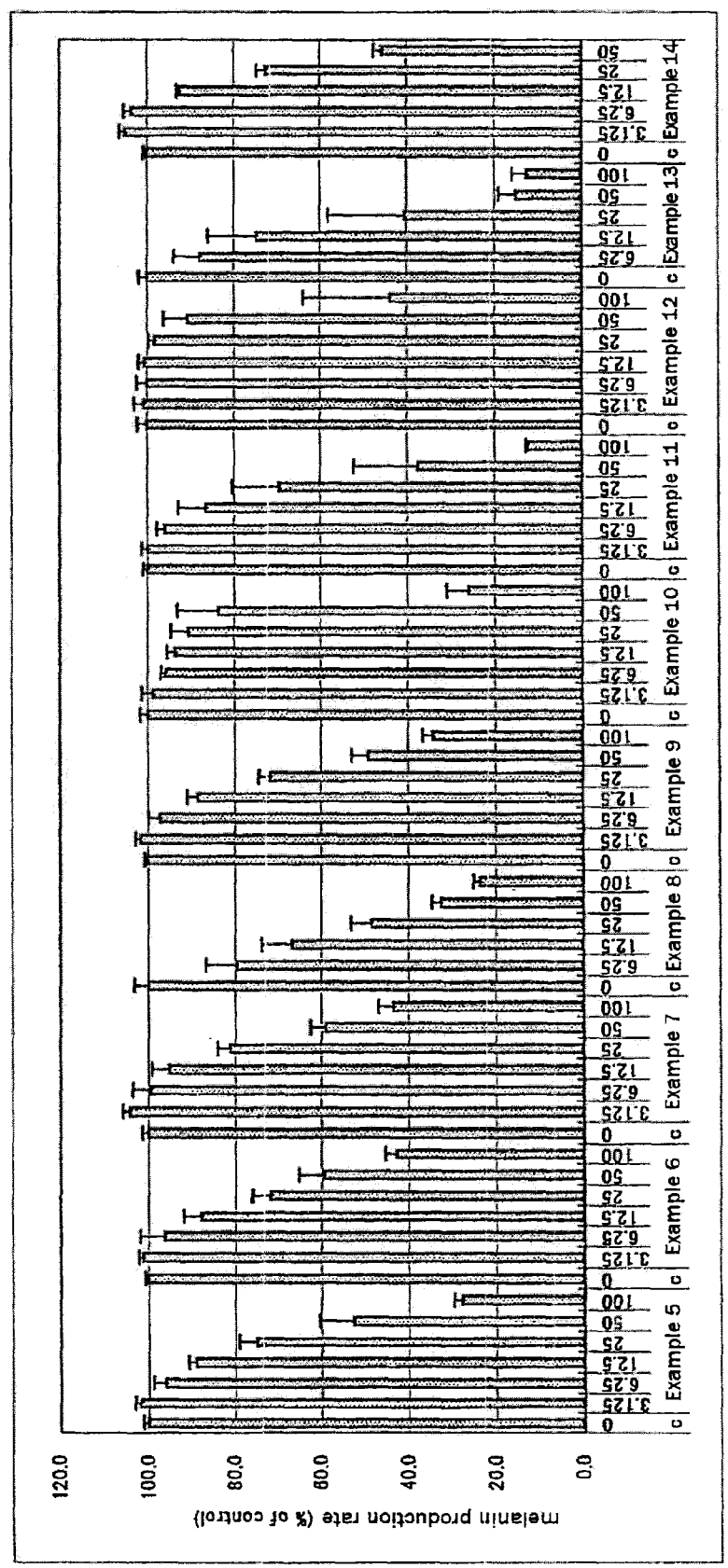
FIG. 2 is a graph showing the results of Experimental example 1. In the graph, the unit of the values on the horizontal axis is μM.
Figure 3:
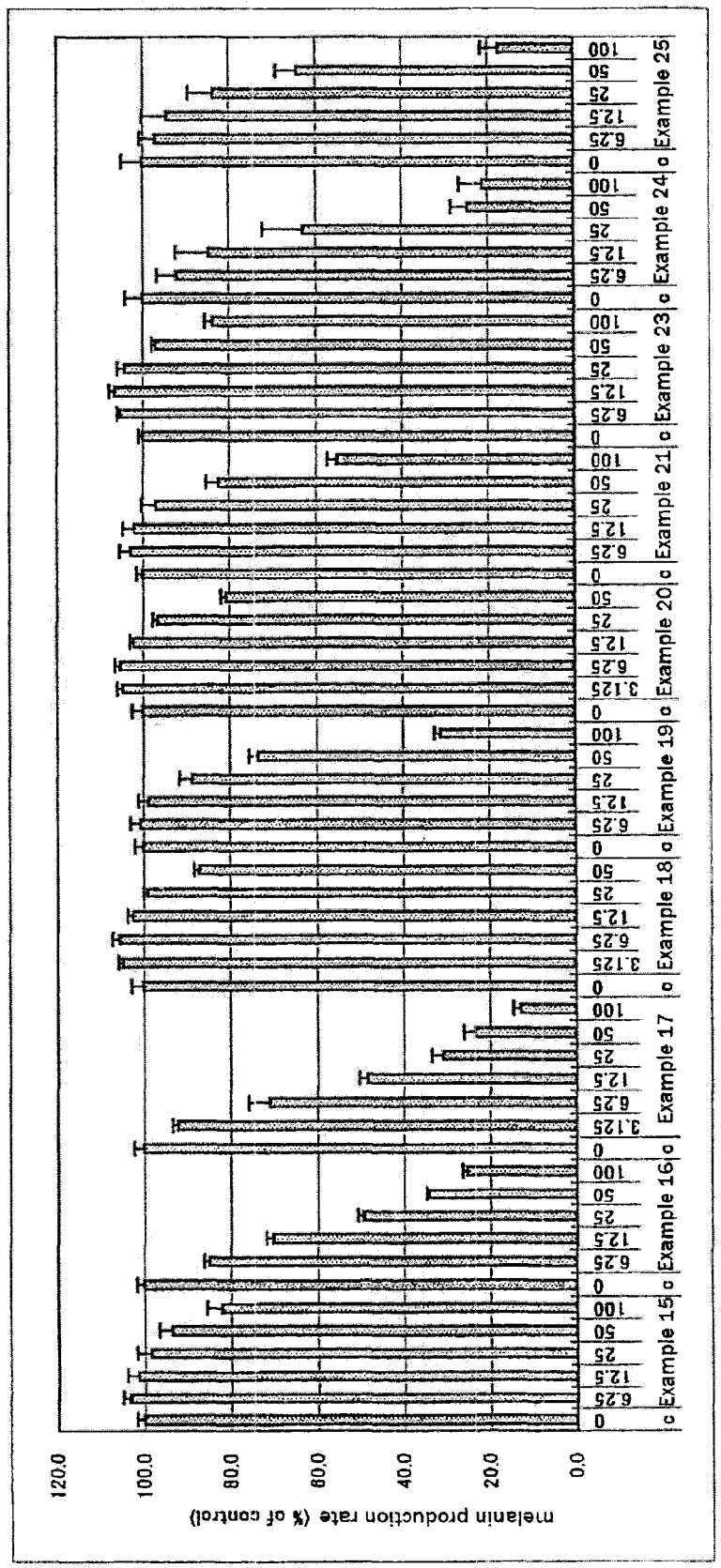
FIG. 3 is a graph showing the results of Experimental example 1. In the graph, the unit of the values on the horizontal axis is μM.
Figure 4:
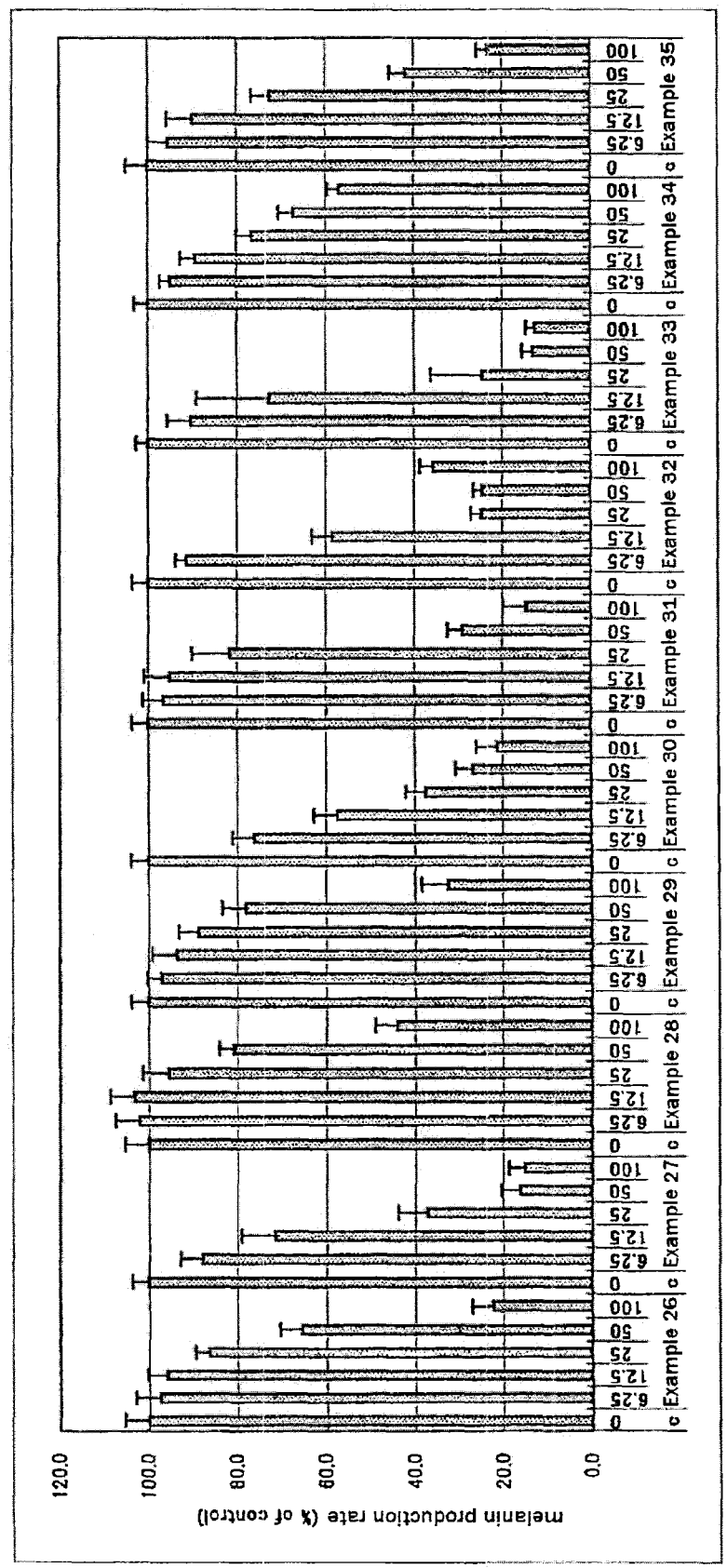
FIG. 4 is a graph showing the results of Experimental example 1. In the graph, the unit of the values on the horizontal axis is μM.
Figure 5:
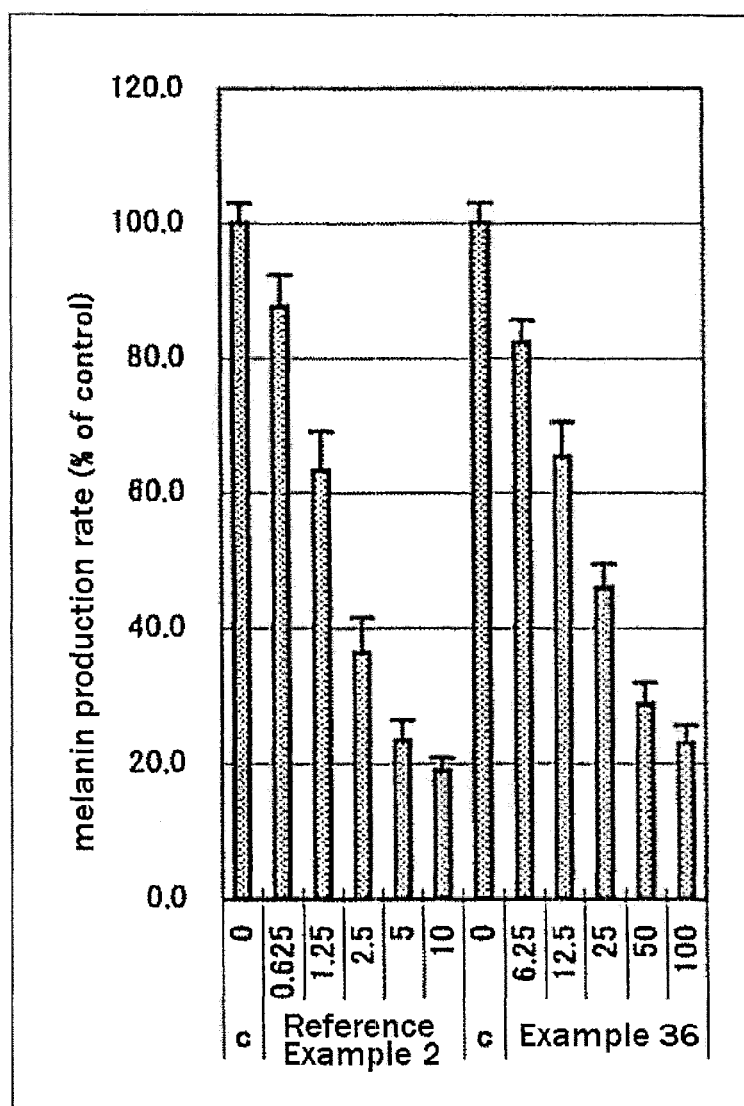
FIG. 5 is a graph showing the results of Experimental example 1. In the graph, the unit of the values on the horizontal axis is μM.

B16 melanom (purchased from Dainippon Sumitomo Pharma Co., Ltd.) was cultured in DMEM (Dulbecco's Modified Eagle Medium, high glucose, containing 10% serum). After confluent, the cells were trypsinized and seeded in a 96-well plate. On the following day, after adhesion of the cells to the plate, the medium was replaced with DMEM containing each evaluation sample (control (no sample addition), sample of each Production Example) at a given evaluation concentration (diluted from 100 μm according to sample), and the cells were incubated for 3 days. The 96-well plate was shaken in a plateshaker for 5 minutes, the absorbance at 450 nm was measured by a microplatereader (Benchmark microplatereader, manufactured by BIORAD), and the amount of melanin in the medium in each well was compared. The absorbance at 3 days after addition of a given concentration of each sample was shown in relative percentage based on the measurement value (absorbance) of control (no sample addition) as 100%. As Comparative Example, a similar test was performed using kojic acid (KoA), 4-hexylresorcinol, CS (N-(p-coumaroyl)serotonin or N-[2-(5-hydroxy-1H-indol-3-yl)ethyl]-3-(4-hydroxyphenyl)-2-propenamide) and FS (N-feruloylcoumaroylserotonin or N-[2-(5-hydroxy-1H-indol-3-yl)ethyl]-3-(4-hydroxy-3-methoxyphenyl)-2-propenamide). The results are shown in FIGS. 1 to 5. The concentration necessary for suppressing production of melanin in each sample by 50%, based on the amount of melanin in the control as 100%, was calculated as 50% melanin production-suppressive concentration IC$_{50}$ (μM). The results are shown in Table 2. As a result, all the compounds of the present invention showed a tendency toward suppression of the amount of melanin. Hence, the compounds of the present invention were shown to be useful as a whitening agent.

Kojic acid (KoA) used was purchased from Sigma-Aldrich Japan K.K., 4-n-hexylresorcinol used was purchased from TOKYO CHEMICAL INDUSTRY CO., LTD., and CS and FS used were synthesized by Ajinomoto Co., Inc.

TABLE 2

| sample | IC$_{50}$ (μM) |
|---|---|
| kojic acid | 315.0 |
| CS | 28.5 |
| FS | 42.4 |
| 4-hexylresorcinol | 23.5 |
| compound of Example 4 | 10.7 |
| compound of Example 13 | 21.5 |
| compound of Example 17 | 14.6 |
| compound of Example 24 | 33.3 |
| compound of Example 30 | 17.1 |
| compound of Reference Example 2 | 1.9 |
| compound of Example 36 | 22.4 |

Experimental Example 2

Cytotoxicity Test

Neutral Red Assay

After measurement of the absorbance in the melanin production suppression test of Experimental Example 1, the evaluation sample solution was removed from the plate, and each well was rinsed with DMEM (200 μl, high glucose, containing 10% serum). A medium containing NR (neutral red) was added to each well at 200 μl/well, and the plate was left standing for 2 hours at 37° C., 5% $CO_2$ under a saturated vapor. The medium was removed, and a washing fixative solution (mixture of equal amounts of 2 wt % calcium chloride solution and 2 wt % formalin solution) was added at 200 μl/well. After 1 minute, the washing fixative solution was removed. An NR extract (acetic acid-ethanol, 200 μl/well) was added, and the mixture was shaken in a plateshaker for 15 minutes. NR uptake by viable cells was examined by measuring the absorbance of the NR extract at 540 nm by a microplatereader (Benchmark microplatereader, manufactured by BIORAD). The cytotoxicity of each sample was calculated as a relative percentage of the absorbance of NR extract of the cells added with a given concentration of each sample to the measurement value (absorbance) of a control NR extract (no sample) as 100%.

As a result, the compounds of Example 32 and Example 33 showed cytotoxicity; however, the compounds of other Examples did not show cytotoxicity. Therefore, it has been demonstrated that the compound of the present invention is promising as a starting material for whitening cosmetics.

INDUSTRIAL APPLICABILITY

The present invention provides a compound having a melanin production suppressive activity, which is useful as a starting material for whitening cosmetics.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method of whitening skin, comprising applying a whitening agent to the skin, wherein said whitening agent comprises a compound represented by formula (V):

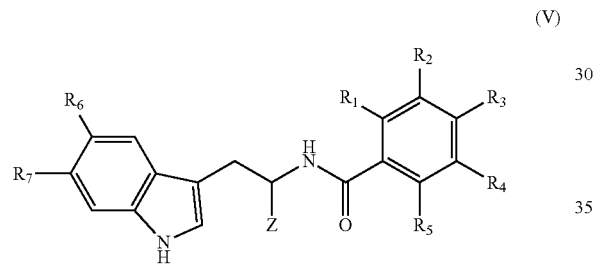

wherein:
$R_1$, $R_2$, $R_3$, $R_4$ and $R_5$ are each independently a hydrogen atom, an alkyl group having a carbon number of 1 to 3, a hydroxyl group or an alkoxy group having a carbon number of 1 to 3, or $R_1$ and $R_2$, or $R_2$ and $R_3$ in combination optionally form a methylenedioxy group, and at least one of $R_1$, $R_2$, $R_3$, $R_4$ and $R_5$ is a hydroxyl group;
$R_6$ is a hydroxyl group and $R_7$ is a hydrogen atom;
Z is a hydrogen atom;
or a salt thereof,
provided that the following compound and salts thereof are excluded:
a compound wherein, when $R_1$, $R_2$ and $R_5$ are hydrogen atoms, then:
$R_3$ and $R_4$ are hydroxyl groups, or
$R_3$ is a hydroxyl group and $R_4$ is a methoxy group,
or $R_3$ and $R_4$ are hydrogen atoms, or
$R_3$ is a methoxy group and $R_4$ is a hydrogen atom.

2. A method of whitening skin, comprising applying a whitening agent to the skin, wherein said whitening agent comprises a compound which is represented by any of formulae (32), (33), (34), (35), or (36):

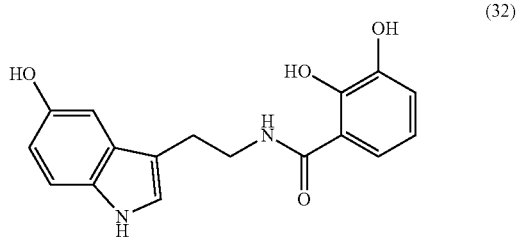

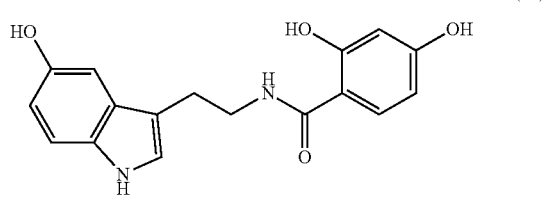

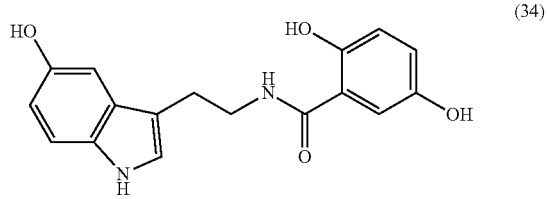

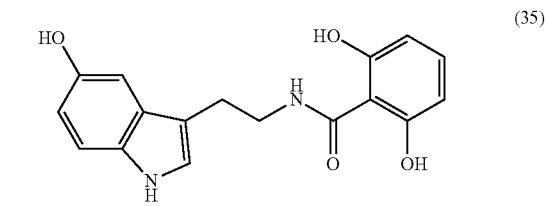

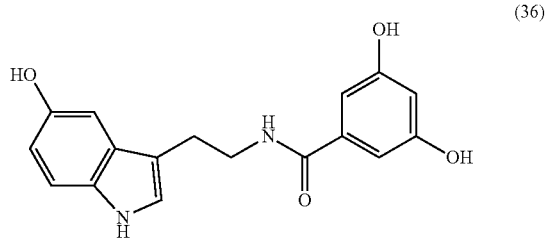

or a salt thereof.

* * * * *